(12) United States Patent
Yashan et al.

(10) Patent No.: US 8,146,431 B2
(45) Date of Patent: Apr. 3, 2012

(54) METHOD AND SYSTEM FOR NON-DESTRUCTIVELY TESTING A METALLIC WORKPIECE

(75) Inventors: Andre Yashan, Saarbrücken (DE); Herbert Willems, Nalbach (DE); Frank Niese, Saarbrücken (DE)

(73) Assignees: NDT Systems & Services AG, Stutensee (DE); Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 664 days.

(21) Appl. No.: 12/086,406

(22) PCT Filed: Nov. 21, 2006

(86) PCT No.: PCT/EP2006/011117
§ 371 (c)(1),
(2), (4) Date: Mar. 27, 2009

(87) PCT Pub. No.: WO2007/068327
PCT Pub. Date: Jun. 21, 2007

(65) Prior Publication Data
US 2009/0301206 A1    Dec. 10, 2009

(30) Foreign Application Priority Data
Dec. 17, 2005 (DE) .................. 10 2005 060 582

(51) Int. Cl.
*G01N 29/07* (2006.01)
(52) U.S. Cl. .......................... 73/643; 73/597
(58) Field of Classification Search ............ 73/643, 73/620, 629, 597, 598, 599; 702/38, 39
See application file for complete search history.

(56) References Cited

U.S. PATENT DOCUMENTS

| | | | | |
|---|---|---|---|---|
| 3,550,435 A | * | 12/1970 | Kaule | 73/617 |
| 4,003,244 A | * | 1/1977 | O'Brien et al. | 73/609 |
| 4,167,878 A | | 9/1979 | Bottcher et al. | |

(Continued)

FOREIGN PATENT DOCUMENTS

DE    31 28 825 A1    3/1983
(Continued)

OTHER PUBLICATIONS

G. Hübschen, et al., Ultraschallprüfung mit Elektromagnetischen Wandlern, FhG-Bericht 1-84.
(Continued)

*Primary Examiner* — J M Saint Surin
(74) *Attorney, Agent, or Firm* — Walter A. Hackler

(57) ABSTRACT

The invention relates to a method for nondestructive testing of a metallic workpiece (11) using an ultrasonic transducer testing head having the following steps: to generate an ultrasonic wave, an excitation pulse is transmitted using the ultrasonic transducer (1) to the workpiece (11), a response signal is measured using the magnetic field sensor (3), testing information, preferably transit time information of the ultrasonic wave and therefrom wall thickness information about the thickness of the workpiece (11), is ascertained on the basis of an ultrasonic echo component of the response signal, and further information, in particular distance information about the distance of the testing head from the workpiece (11), is ascertained on the basis of a magnetic field component of the response signal by supplementary analysis. The invention also relates to a corresponding analysis method for analyzing measurement data which has been ascertained using an ultrasonic transducer testing head and a system for nondestructive testing of a metallic workpiece.

9 Claims, 2 Drawing Sheets

U.S. PATENT DOCUMENTS

| | | | | |
|---|---|---|---|---|
| 4,173,898 | A | * | 11/1979 | Forstermann et al. .......... 73/611 |
| 4,437,332 | A | * | 3/1984 | Pittaro ............................ 73/597 |
| 4,727,321 | A | | 2/1988 | Hüschelrath |
| 4,769,598 | A | * | 9/1988 | Krieg et al. ................... 324/219 |
| 6,009,756 | A | * | 1/2000 | Willems et al. ................. 73/643 |
| 6,479,992 | B2 | * | 11/2002 | Kato et al. .................... 324/232 |
| 7,024,935 | B2 | * | 4/2006 | Paige et al. ..................... 73/643 |

FOREIGN PATENT DOCUMENTS

| | | |
|---|---|---|
| DE | 0 200 183 A2 | 11/1986 |
| DE | 35 30525 A1 | 11/1986 |
| DE | 31 53 252 C2 | 6/1989 |
| EP | 0 071 147 B1 | 4/1985 |
| EP | 0 200 183 A2 | 11/1986 |
| EP | 0 276 299 B1 | 11/1993 |
| EP | 0 677 472 B1 | 10/1995 |
| EP | 0 677 742 A1 | 10/1995 |
| EP | 0 717 842 B1 | 6/1996 |
| EP | 0 775 910 A1 | 5/1997 |
| GB | 2 120 789 A | 12/1983 |
| GB | 120789 A2 | 12/1983 |

OTHER PUBLICATIONS

G. Hüuschelrath, Combined Rotating EMAT Wall Thickness Measuring and Flux Leakage Defect Detection System for In-Line Tube Testing, 1985.
Igarashi, Alers IEEE Ultrasonics Symposium 1998-893.
K. Reber, New Developments in MFL-Pipeline Inspection Technology, proc. NDT iin Progress Meeting, Trest 2001.
R. Bickerstaff, et al., Review of Sensor Technologies for in line-Inspection.
V.K. Varma, State-of-the-Art Natural Gas Pipeline Inspection.
Hueschelrath, G: "Combined Rotating EMAT wall Thickness Measuring and Flux Leakage Defect Detection System for In-Line Tube Testing", 1985 Int. Committee on Nondestructive Testing, Columbus, OH, USA, 1985, pp. 1830-1837, XP009078133.

* cited by examiner

METHOD AND SYSTEM FOR NON-DESTRUCTIVELY TESTING A METALLIC WORKPIECE

The invention relates to a method for nondestructive testing of a metallic workpiece using a testing head, which has an electromagnetic ultrasonic transducer having a magnetic field source and a magnetic field sensor. The invention also relates to an analysis method for analyzing measurement data which have been ascertained using a testing head of this type, and a testing system.

Nondestructive testing is of great significance in particular for pipelines, such as natural gas or petroleum pipelines. According to the prior art, pigs having testing heads are used for this purpose, which have an ultrasonic transducer, using which ultrasonic waves may be generated and ultrasonic echoes may be detected. By analyzing the ultrasonic echoes, transit time information of the ultrasonic waves may be ascertained and the wall thickness may be calculated therefrom. In this manner, corrosion points and other defects which result in a reduced wall thickness may be recognized.

In addition to electromagnetic ultrasonic transducers, with which ultrasonic waves are generated directly in the workpiece to be tested, piezoelectric ultrasonic transducers are known in the prior art, with which ultrasonic waves are generated outside the workpiece and coupled into the workpiece using coupling means.

Piezoelectric ultrasonic transducers have the advantage that when the ultrasonic waves are coupled into the workpiece to be tested, an entry echo results, using which the distance of the testing head to the workpiece may be ascertained. If an electromagnetic ultrasonic transducer is used, no such entry echo results, so that only the thickness of the workpiece, but not its distance from the testing head may be ascertained by a transit time analysis.

In liquid-filled pipelines, such as petroleum pipelines, the liquid present is available as the coupling means, so that the use of piezoelectric ultrasonic transducers is possible with relatively few problems. In gas-filled pipelines, such as natural gas pipelines, it is only possible to couple in ultrasonic waves and thus use piezoelectric ultrasonic transducers with very great effort or not at all. Therefore, it was suggested in EP 0 775 910 E1 that electromagnetic ultrasonic transducers be used for applications of this type.

However, if electromagnetic ultrasonic transducers are used, it is not possible to differentiate between internal or external flaws of a pipeline, because no entry echo results and therefore no information about the distance of the testing head from the surface of the workpiece to be tested may be obtained by analyzing the ultrasonic echo. A further problem if electromagnetic ultrasonic transducers are used is that the signal-to-noise ratio worsens drastically with increasing distance of the testing head from the workpiece, so that a transit time analysis is typically only possible if the distance of the testing head from the workpiece is less than approximately 1 mm. If depressions have formed due to internal corrosion in a pipeline, the distance of the ultrasonic testing head from the wall to be measured may become so great that a reliable statement about the wall thickness is no longer possible.

For many applications, in particular for examining pipelines, it is desirable to be able to differentiate between internal and external flaws. Therefore, there is a need for a testing head, using which distance information about the distance of the testing head from the workpiece may be ascertained in addition to wall thickness information, because in an area having internal flaws, the distance of the testing head from the wall is increased by the depth of the flaw.

To solve this problem, it is suggested in EP 0677742 A1 that an eddy current measurement additionally be performed in measurement pauses of the ultrasonic transducer. In eddy current testing, an electromagnetic alternating field is generated using a transmitting coil, which is influenced by the electrical conductivity, the magnetic permeability, and the geometry of the workpiece to be tested. This alternating field may be measured using a magnetic field sensor which is positioned adjacent to the transmitting coil and the distance from the workpiece to be tested may be ascertained. If the distance is too great for an ultrasonic echo analysis because of an internal flaw, the wall thickness may be ascertained as the difference between the wall thickness of an undamaged area and the additional distance of the testing head from the damaged wall.

However, an essential disadvantage of the method known from EP 0677742 A1 is that the time required for testing a workpiece approximately doubles due to the eddy current measurements performed between the ultrasonic measurements. In addition, there is a significant outlay for apparatus.

Furthermore, combining ultrasonic measurements with leakage flux measurements for testing ferromagnetic materials is known from DE 31 53 252 C2 and DE 31 28 825 C2. A magnetic field is used which is generated by a magnet rotating around the testing body, which encloses the testing body using two pole shoes. A measurement apparatus which combines leakage flux and ultrasonic measurements is also known from GB 2 120 789 A. In this measurement apparatus, the workpiece to be studied is also positioned between the pole shoes of a permanent magnet and a leakage flux detector is used for the measurement of the leakage flux and an appropriately adapted coil is used for the measurement of the ultrasonic signal. A device for detecting cracks using an electromagnetic transient diffusion method is known from EP 0 717 842 B1, in which magnetic variables are measured. Separate probes are used for the leakage flux and eddy current measurements, but no ultrasonic measurement.

The checking of composite materials by a combined application of pulse eddy current and piezoelectrically generated ultrasound is known from EP 0 276 299 B1, separate probes being used for the eddy current and ultrasonic measurements.

The object of the invention is therefore to specify a way in which a gas-filled pipeline may be checked and internal flaws may be differentiated from external flaws with less effort.

SUMMARY OF THE INVENTION

This object is achieved by a method for nondestructive testing of a metallic workpiece using a testing head which has an electromagnetic ultrasonic transducer having a magnetic field source and a magnetic field sensor, the method comprising the following steps:

an excitation pulse is transmitted to the workpiece using the ultrasonic transducer to generate an ultrasonic wave, a response signal is measured using the magnetic field sensor, testing information, preferably transit time information of the ultrasonic wave is ascertained on the basis of an ultrasonic echo component of the response signal, and wall thickness information about the thickness of the workpiece is ascertained therefrom, and further information, in particular wall thickness information or distance information about the distance of the testing head from the workpiece, is ascertained on the basis of a magnetic field component of the response signal by a supplementary analysis.

In the method according to the invention, it is possible to differentiate between internal and external flaws of a pipeline from a single response signal, which is generated by a signal excitation pulse, by analyzing various signal components. An essential advantage of the method according to the invention is that no additional measuring time in comparison to typical ultrasonic measurements using electromagnetic ultrasonic transducers is required for ascertaining the wall thickness information due to the improved signal analysis. Therefore, a pipeline may be checked in essentially the same time using a testing head which was already required according to the prior art for an ultrasonic wall thickness measurement, although it is possible to differentiate between internal and external flaws by additional information according to the invention.

While according to the prior art only the ultrasonic echo component of a response signal is analyzed and wall thickness information is ascertained therefrom, in the method according to the invention, a magnetic field component of the response signal is additionally analyzed and further information for differentiating between internal and external flaws is ascertained therefrom. Specifically, it was recognized in the context of the invention that the response signal obtained upon an ultrasonic echo measurement using an electromagnetic ultrasonic transducer also contains a stray field component and an alternating field component as magnetic field components in addition to the ultrasonic echo component, by whose analysis in combination with the analysis of the ultrasonic echo component, distance information and/or wall thickness information may be obtained.

The stray field component is based on leakage flux of the magnetic field generated by the magnetic field source. To obtain a maximum leakage flux signal, a testing head is preferably used in which the magnetic field sensor is positioned between a magnetic north pole and a magnetic south pole of the magnetic field source on a front face of the testing head, wherein the front face of the testing head faces toward the workpiece during performance of the method. The magnetic north pole and the magnetic south pole of the magnetic field source cause a magnetization of the workpiece in the longitudinal direction in this way. Stray fields form in the area of wall thickness reductions, which may be detected by the magnetic field sensor of the testing head. If an increased stray field component is established with vanishing ultrasonic component, this indicates an internal flaw. If an increased stray field component occurs together with a strong ultrasonic component, there is an external flaw.

If the testing head is at rest in relation to the workpiece, the stray field is constant over time. A time dependence of the stray field first occurs due to a movement of the testing head in relation to the workpiece. Even if a pig having a testing head is moved relatively rapidly through a pipeline, the frequency of the measured stray field is significantly less than the frequency of the ultrasonic signal contained in the response signal. The leakage flux component of the response signal may therefore be ascertained by frequency filtering and be separately analyzed to obtain wall thickness information independent of the ultrasonic measurement.

Analysis of the stray field component is also possible with testing heads which only have a single coil which is used both as an excitation coil for generating the excitation pulse and also as a magnetic field sensor for detecting the response signal. The testing head used for the invention preferably also has an excitation coil in addition to the magnetic field sensor, using which the excitation pulse is generated and which is positioned between the north pole and the south pole of the magnetic field source adjacent to the magnetic field sensor.

The magnetic field component of the response signal also contains an alternating field component of an alternating field generated through the excitation pulse by the excitation coil. Specifically, an alternating current flows through the excitation coil to generate the excitation pulse, so that a magnetic alternating field is generated which causes an alternating field component of the magnetic field component of the response signal. The alternating field component occurs practically simultaneously with the excitation pulse, so that the alternating field component may be separated from the ultrasonic echo component of the response signal by suitable selection of the chronological analysis interval. Therefore, a first time interval and a second time interval are analyzed separately to analyze the response signal, the alternating field component being ascertained by analyzing the first time interval and the ultrasonic echo component being ascertained by analyzing the second time interval.

The principles of eddy current testing may be used for analyzing the alternating field component. In eddy current testing, an electrical current of strength I and frequency $\omega=2\pi f$ flows in a transmitting coil (whose function is assumed here by the excitation coil) and thus generates an electromagnetic alternating field in the environment, i.e., also at the location of a magnetic field sensor and in a testing body. This alternating field is influenced by the electrical conductivity $\sigma$, the magnetic permeability $\mu$, and the geometry of the testing body, in particular the distance between testing body and sensor. By analyzing the alternating field component, the distance of the testing head from the workpiece and/or other workpiece parameters may thus be determined upon suitable calibration.

In principle, analysis of the alternating field component is also possible with testing heads which only have a single coil which is used both as the excitation coil for generating the excitation pulse for the ultrasonic and eddy current measurements and also as the magnetic field sensor. The impedance of the excitation coil is a function of the distance between testing head and workpiece, so that the alternating field component may also be ascertained by an impedance measurement of the excitation coil. However, a testing head which has a magnetic field sensor in addition to the excitation coil is preferably used.

Both the stray field component and also the alternating field component of the response signal are preferably analyzed. An overall observation of the analysis results of the stray field component, the alternating field component, and the ultrasonic echo component allows especially comprehensive information about the condition of the workpiece to be tested to be obtained.

The advantages of the described invention are essentially also achieved by a novel analysis of the response signals measured using a testing head. The invention therefore also relates to an analysis method for analyzing measurement data which has been ascertained using a testing head for nondestructive testing of a metallic workpiece, the testing head used having an electromagnetic ultrasonic transducer having a magnetic field source and a magnetic field sensor, an excitation pulse being transmitted to the workpiece to generate an ultrasonic wave using the ultrasonic transducer, and a response signal being measured using the magnetic field sensor, testing information, preferably transit time information of the ultrasonic waves, and therefrom wall thickness information about the thickness of the workpiece, being ascertained on the basis of an ultrasonic echo component of the response signal, and further information, in particular wall thickness information or distance information about the distance of the testing head from the workpiece, being ascertained on the basis of a magnetic field component of the response signal.

Because extensive calculations are required for analyzing the response signals, the use of an electronic data processing facility is recommended. The invention therefore also relates to a computer program product which may be loaded directly into the memory of a digital computer and comprises software sections, using which the steps of an analysis method of this type may be executed when the product runs on a computer. The invention also relates to a computer-capable storage medium, such as a CD, DVD, or hard drive, on which such a computer program product is stored.

The object stated at the beginning is also achieved by a system for nondestructive testing of a metallic workpiece using the method according to the invention, comprising a testing head, which has an electromagnetic ultrasonic transducer having a magnetic field source and a magnetic field sensor, a memory for storing a response signal which was measured using the magnetic field sensor following the generation of an excitation pulse exerted on the workpiece using the ultrasonic transducer, and an analysis unit, which is set up to analyze the response signal by applying the analysis method according to the invention.

BRIEF DESCRIPTION OF THE DRAWINGS

Further details and advantages of the invention are explained on the basis of an exemplary embodiment with reference to the appended drawings. The features described therein may be used individually or in combination to provide preferred embodiments of the invention. In the figures.

DETAILED DESCRIPTION

Figure 1:
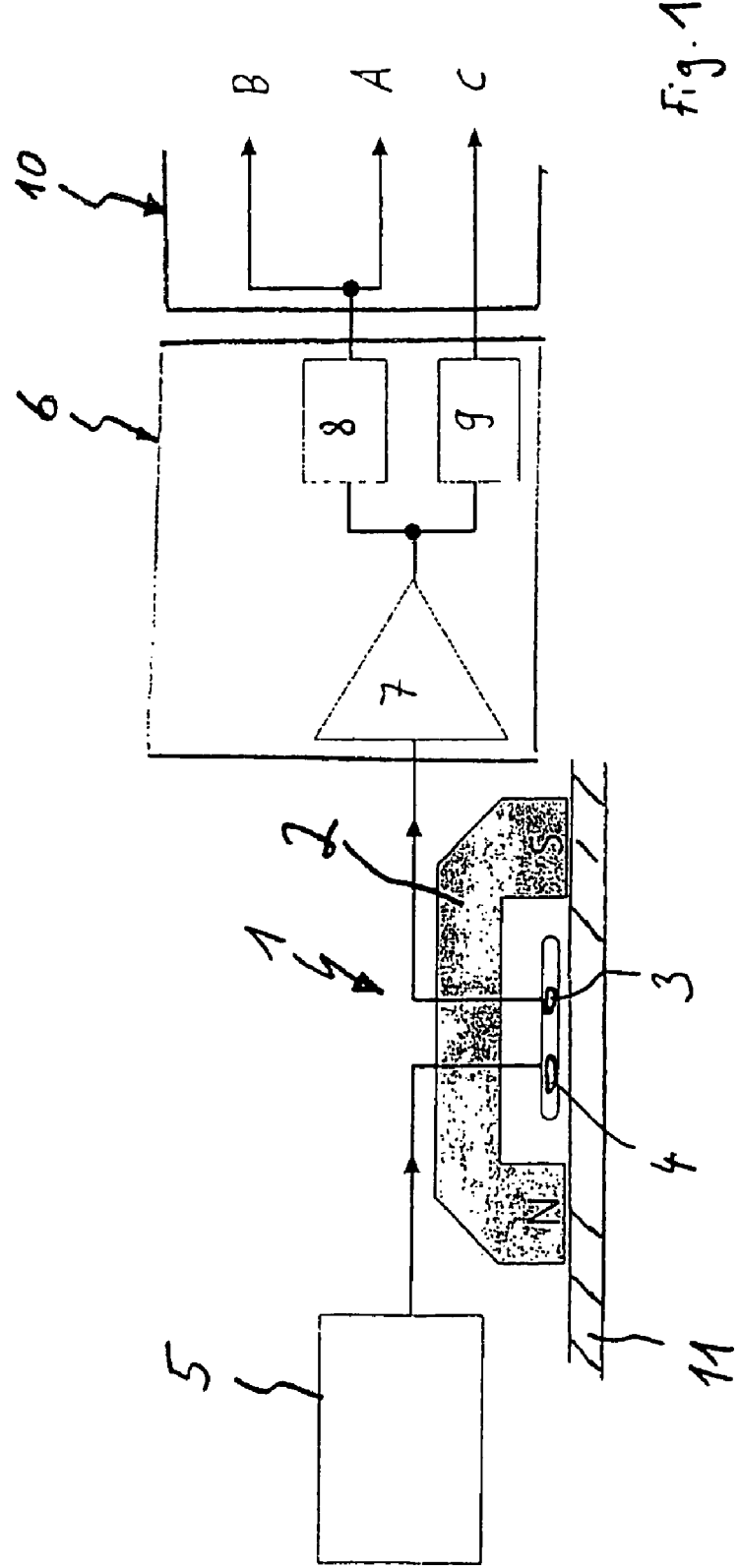
FIG. 1 shows a schematic illustration of a testing system according to the invention.

FIG. 1 shows a schematic sketch of a system for nondestructive testing of a metallic workpiece. The system comprises a testing head which has an ultrasonic transducer 1 having a magnetic field source 2, a magnetic field sensor 3 in the form of a coil, and an excitation coil 4. The magnetic field sensor 3 and the excitation coil 4 are positioned between a magnetic north pole N and a magnetic south pole S of the magnetic field source 2 on a front face of the testing head, wherein the front face of the testing head faces toward the workpiece 11 to be tested in operation of the testing head.

In the exemplary embodiment shown, the magnetic field source 2 is implemented as a permanent magnet having a U-shaped pole shoe. In this manner, a workpiece to be tested is magnetized in a longitudinal direction, so that a course of field lines running essentially parallel to the surface of the workpiece 11 results. To generate a course of field lines of this type, for example, a magnetic field source having two rod-shaped permanent magnets may also be used, between which the magnetic field sensor 3 and the excitation coil 4 are positioned, one of these permanent magnets being positioned having its north pole on the front face of the testing head and the other magnet having its south pole on the front face.

An electromagnet may also be used as the magnetic field source. A coil is preferably used as the magnetic field sensor 3, other magnetic field sensors also possibly being suitable, however.

To generate an ultrasonic wave, an excitation pulse is transmitted to the workpiece using the electromagnetic ultrasonic transducer 1. The excitation coil 4 is connected to activation electronics 5 for this purpose, using which the excitation pulse is generated and transmitted to the excitation coil 4. The frequency of the excitation pulse corresponds to the frequency of the ultrasonic wave to be generated and is typically at approximately 0.5 MHz to 10 MHz. The duration of the excitation pulse is a few oscillation cycles. For example, an excitation pulse having a frequency of 2 MHz and a duration of 1 μs to 10 μs, preferably 2 μs to 6 μs, may be used to test a pipeline. In order that the ultrasonic wave generated using the excitation pulse has sufficient intensity to allow ultrasonic echoes having an advantageous signal-to-noise ratio to be identified in a response signal, a voltage of at least 0.5 kV, preferably 1 kV to 5 kV, especially preferably 2 kV to 4 kV is used for the excitation pulse. The activation electronics 5 are preferably powered by a battery so that the testing head may also be used on a pig for testing pipelines.

The excitation pulse is transmitted by the excitation coil to the workpiece to be tested as a high-frequency alternating field. In ferromagnetic workpieces, as are typically used as steel for pipelines, this magnetic alternating field causes a magnetostrictive excitation of an ultrasonic wave. The magnetic field generated by the magnetic field source is used for setting a favorable magnetostrictive operating point. The magnetic field generated by the magnetic field source 2 is modulated around this operating point using the excitation pulse of the excitation coil 4.

In metallic workpieces which are not ferromagnetic, the alternating field of the excitation coil 4 causes ultrasound generation due to the Lorenz force which acts on eddy currents induced by the excitation pulse. Ultrasonic excitation by Lorenz forces also occurs in principle in ferromagnetic materials, but the magnetostrictive excitation mechanism is significantly more efficient, so that the excitation via Lorenz forces is rather insignificant in practice in ferromagnetic materials. Because an ultrasonic excitation via Lorenz forces is less efficient than a magnetostrictive ultrasonic excitation, greater voltages are required for the excitation pulse generated by the excitation electronics 5 in non-ferromagnetic materials.

Following the transmission of the excitation pulse to the workpiece, a response signal is measured using the magnetic field sensor 3. The magnetic field sensor 3 is connected to analysis electronics 6, using which a pre-analysis of the response signal is performed. The analysis electronics 6 comprise a preamplifier 7, a high-pass filter 8, and a low-pass filter 9. The response signal is first amplified using the preamplifier 7 and subsequently supplied to the inputs of the high-pass filter 8 and the low-pass filter 9, which are connected in parallel. The high-pass filter 8 has a cutoff frequency between 10 kHz and 500 kHz, preferably between 100 kHz and 200 kHz, so only those parts of the response signal whose frequency is greater than the cutoff frequency of the high-pass filter 8 and which therefore contain the ultrasonic echo component arrive at the output of the high-pass filter 8. The cutoff frequency of the low-pass filter 9 is preferably between 5 kHz and 500 kHz, more preferably between 5 kHz and 100 kHz, in particular between 10 kHz and 50 kHz, so that only signal components of the response signal whose frequency is less than the cutoff frequency of the low-pass filter 9 and which therefore contain the stray field component arrive at the output of the low-pass filter.

The analysis electronics 6 are connected to an analysis unit 10, using which wall thickness information about the thickness of the workpiece and distance information about the distance of the testing head from the workpiece are ascertained. The analysis electronics 6 may also be connected to a memory, which the analysis unit 10 may access. In this manner it is possible to also position the analysis unit 10 outside the testing head and implement it as a PC, for example. Measurement data obtained using the testing head may be provided to the analysis unit 10 and analyzed at an arbitrary time after the measurement.

In the analysis of the response signal, wall thickness information about the thickness of the workpiece is ascertained on the basis of an ultrasonic echo component. In addition, second independent wall thickness information and distance information about the distance of the testing of the workpiece are ascertained on the basis of a magnetic field component of the response signal.

The magnetic field component of the response signal used for ascertaining the further information contains a stray field component, which is based on the leakage flux, exiting from the workpiece 11, of the magnetic field generated by the magnetic field source 2. This stray field component is ascertained using the low-pass filter 9 by frequency filtering of the response signal. If the testing head is at rest in relation to the workpiece, the stray field component of the response signal is also constant over time. With moving testing head, the stray field component is time-dependent, but its frequency is less than 10 kHz even upon rapid movement of the testing head.

Figure 2:
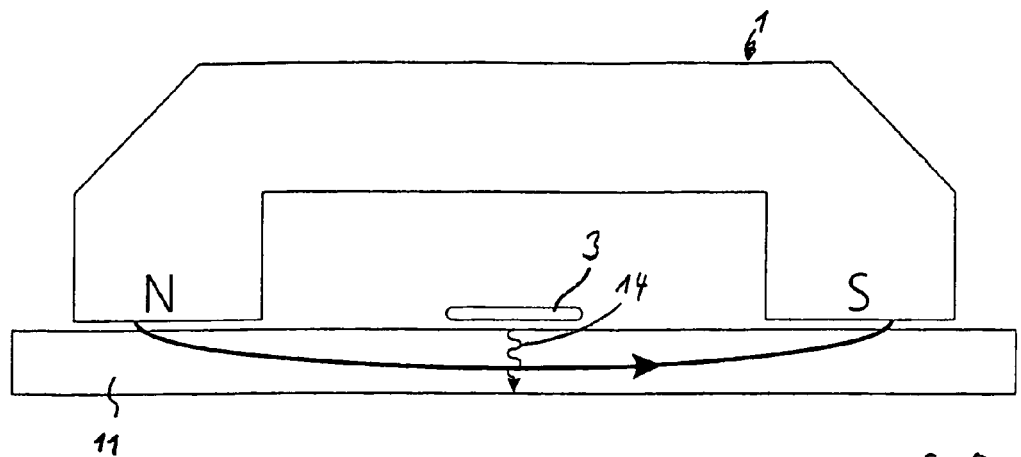
FIG. 2 shows a testing head of the system shown in FIG. 1 including the course of field lines during testing of an intact wall section.
Figure 3:
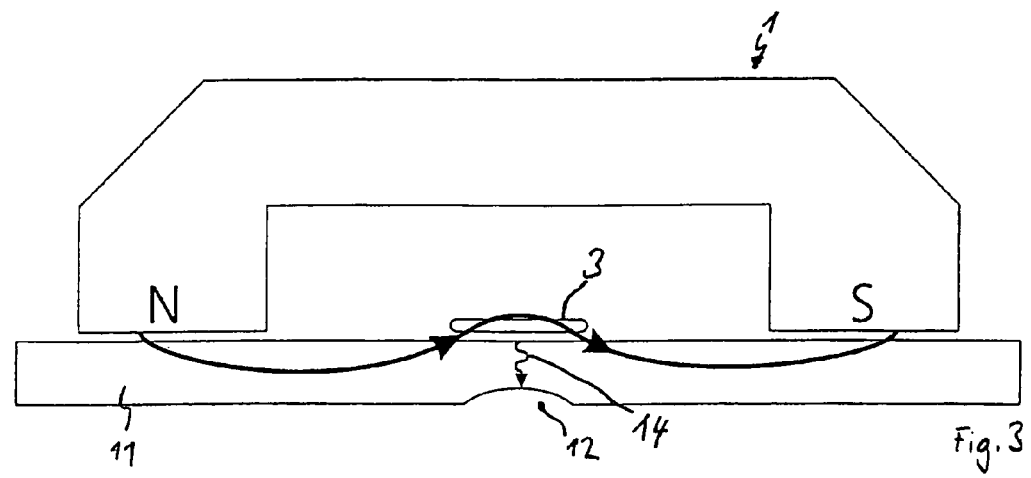
FIG. 3 shows the testing head from FIG. 2 during testing of a wall section having an internal flaw.
Figure 4:
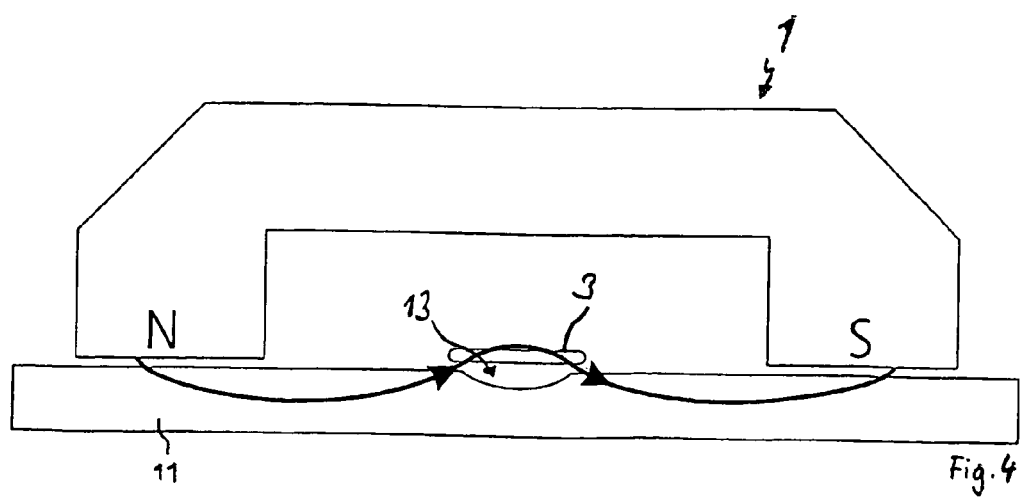
FIG. 4 shows the testing head from FIG. 2 during testing of a wall section having an external flaw.

The principle of a stray field measurement is explained hereafter on the basis of FIGS. 2 to 4, which show an ultrasonic transducer 1 during generation of an ultrasonic wave 14 in the workpiece 11. During testing of an intact pipe wall section, the course of the field lines shown in FIG. 2 results, in which the field lines run essentially inside the workpiece 11 and practically no leakage flux occurs. If the thickness of the workpiece 11 is reduced by a defect 12, 13, the field lines are displaced out of the workpiece 11 at the corresponding point, so that a stray field occurs, which may be detected by the magnetic field sensor 3. If the testing head 1 is located on a pig, the course of field lines shown in FIG. 3 results in the event of an external defect 12 of the pipeline to be tested. The course of field lines shown in FIG. 4 accordingly results in the event of an internal defect 13.

While the external defect 12 shown in FIG. 3 may be recognized by analyzing the ultrasonic echo component of the response signal on the basis of the reduced wall thickness, this is not possible with the internal defect 13 shown in FIG. 4. Specifically, an increased distance results between the excitation coil 4 and the surface to be tested of the workpiece 11 as a result of the defect 13, by which the transmission of the excitation pulse to the workpiece 11 is obstructed.

A more precise and comprehensive statement about the condition of the studied workpiece may be made in that both the ultrasonic echo component and also the stray field component of the response signal are analyzed. It is important in this context that a simplified testing head may be used for measurement of this type, in which the excitation coil 4 is concurrently also used as the magnetic field sensor 3. However, a testing head of the type shown in FIG. 1 in which an excitation coil 4 and, in addition, a magnetic field sensor 3 in the form of a further coil are provided is preferred.

Distance information about the distance of the testing head from the workpiece 11 may be ascertained by an eddy current measurement. For this purpose, it is necessary for a magnetic field sensor 3 to be positioned adjacent to the excitation coil 4. In the method described hereafter, the excitation pulse is used both for the ultrasonic echo measurement and also for the eddy current measurement. The response signal measured using the magnetic field sensor 3 contains, in addition to the ultrasonic echo component, a magnetic field component which includes an alternating field component, caused by an eddy current, of an alternating field generated by the excitation pulse of the excitation coil 4.

The strength of the alternating field component at the location of the magnetic field sensor 3 is a function on one hand of workpiece-independent parameters (e.g., current strength of the excitation pulse, geometry and turn number of the excitation coil) and on the other hand of workpiece-dependent parameters. The workpiece-dependent parameters include, in addition to the electrical conductivity and the magnetic permeability, the distance between the workpiece and the ultrasonic transducer 1 in particular. Therefore, distance information may be obtained by analyzing the alternating field component of the response signal.

The alternating field component of the response signal caused by the eddy current has the frequency of the excitation pulse, like the ultrasonic echo component of the response signal, and is therefore also applied at the output of the high-pass filter 8. In contrast to the ultrasonic echo component, however, the alternating field component occurs quasi-simultaneously with the excitation pulse. Therefore, the alternating field component of the response signal may be separated easily from the ultrasonic echo component, which first occurs with a time delay, caused by transit time, which is a function of the wall thickness, by suitable selection of the chronological analysis window.

Preferably, a first time interval and a second time interval are analyzed separately to analyze the response signal, the alternating field component being ascertained by analyzing the first time interval and the ultrasonic echo component being ascertained by analyzing the second time interval. A duration of less than 3 μs measured from the beginning of the excitation pulse is typically sufficient for the first time interval. Longer times may also be selected for the first time interval, it being ensured, however, that no ultrasonic echo components are contained in the first time interval, i.e., the duration of the first time interval, measured from the excitation pulse, is less than the duration until the occurrence of the first ultrasonic echo.

The splitting of the response signal into an ultrasonic echo component and an alternating field component caused by the eddy current is performed by the analysis unit 10. By applying the described analysis method, the response signal is divided into an ultrasonic echo component A and a magnetic field component, which contains an alternating field component B and a stray field component C.

By analyzing the individual components, both wall thickness information about the thickness of the workpiece and also distance information about the distance of the testing head to the workpiece are ascertained.

What is claimed is:

1. A method for nondestructive testing of a metallic workpiece (11) using a testing head,
   which has an electromagnetic ultrasonic transducer (1) having a magnetic field source (2) and a magnetic field sensor (3),
   wherein the method comprises the following steps:
   an excitation pulse is transmitted using the ultrasonic transducer (1) to the workpiece (11) to generate an ultrasonic wave, a response signal is measured using the magnetic field sensor (3), testing information, preferably transit time information of the ultrasonic wave, is ascertained on the basis of an ultrasonic echo component of the response signal measured by the magnetic field sensor (3), and wall thickness information about the thickness of the workpiece (11) is ascertained therefrom, and further information, wherein wall thickness information and distance information about the distance of the testing head from the workpiece (11) is ascertained by a supplementary analysis on the basis of a magnetic field component of the response signal measured by the magnetic field sensor (3), wherein the testing head used has an excitation coil (4), using which the excitation pulse is generated, the magnetic field component used to ascertain the further information, in particular the distance information, containing an alternating field component of an alternating field generated by the excitation coil and the alternating field component being analyzed to ascertain the distance information.

2. The method according to claim 1, characterized in that a first time interval and a second time interval are analyzed separately to analyze the response signal measured by the magnetic field sensor (3), the alternating field component being ascertained by analyzing the first time interval and the ultrasonic echo component being ascertained by analyzing the second time interval.

3. The method according to claim 1, characterized in that the magnetic field sensor (3) is positioned between a magnetic north pole (N) and a magnetic south pole (S) of the magnetic field source (2) on a front face of the testing head, wherein the front face of the testing head faces toward the workpiece (11) during performance of the method.

4. The method according to claim 3, characterized in that the magnetic field component of the response signal used to ascertain the further information contains a stray field component which originates from the leakage flux exiting from the workpiece (11) of the magnetic field generated by the magnetic field source (2), the stray field component being analyzed to ascertain wall thickness information.

5. The method according to claim 4, characterized in that the magnetic field component of the response signal originating from the leakage flux is ascertained by frequency filtering of the response signal.

6. An analysis method for analyzing measurement data, which has been ascertained using a testing head for nondestructive testing of a metallic workpiece, wherein the testing head used has a electromagnetic ultrasonic transducer (1) having a magnetic field source (2) and a magnetic field sensor (3), an excitation pulse is transmitted using the ultrasonic transducer (1) to the workpiece (11) to generate an ultrasonic wave, and a response signal is measured using the magnetic field sensor (3), testing information, preferably transit time information of the ultrasonic wave and therefrom wall thickness information about the thickness of the workpiece (11) being ascertained on the basis of an ultrasonic echo component of the response signal measured by the magnetic field sensor (3), and further information, wherein wall thickness information and distance information about the distance of the testing head from the workpiece (11), being ascertained on the basis of a magnetic field component of the response signal measured by the magnetic field sensor (3), and wherein the testing head used has an excitation coil (4), using which the excitation pulse is generated, the magnetic field component used to ascertain the further information, in particular the distance information, containing an alternating field component of an alternating field generated by the excitation coil and the alternating field component being analyzed to ascertain the distance information.

7. The method according to claim 6 further comprising carrying out the method on a computer.

8. The method according to claim 7 further providing a computer-capable storage medium.

9. A system for nondestructive testing of a metallic workpiece using a method for nondestructive testing of a metallic workpiece (11) using a testing head, which has an electromagnetic ultrasonic transducer (1) having a magnetic field source (2) and a magnetic field sensor (3), wherein the method comprises the following steps:

an excitation pulse is transmitted using the ultrasonic transducer (1) to the workpiece (11) to generate an ultrasonic wave, a response signal is measured using the magnetic field sensor (3), testing information, preferably transit time information of the ultrasonic wave, is ascertained on the basis of an ultrasonic echo component of the response signal measured by the magnetic field sensor (3), and wall thickness information about the thickness of the workpiece (11) is ascertained therefrom, and further information, wherein wall thickness information and distance information about the distance of the testing head from the workpiece (11) is ascertained by a supplementary analysis on the basis of a magnetic field component of the response signal measured by the magnetic field sensor (3), wherein the testing head used has an excitation coil (4), using which the excitation pulse is generated, the magnetic field component used to ascertain the further information, in particular the distance information, containing an alternating field component of an alternating field generated by the excitation coil and the alternating field component being analyzed to ascertain the distance information, the system comprising:

a testing head, which has an electromagnetic ultrasonic transducer (1) having a magnetic field source (2) and a magnetic field sensor (3), a memory for storing a response signal, which is measured using the magnetic field sensor (3) following the generation of an excitation pulse exerted on the workpiece using the ultrasonic transducer, and an analysis unit (10), which is set up to analyze the response signal by use of an analysis method for analyzing measurement data, which has been ascertained using a testing head for nondestructive testing of a metallic workpiece, wherein the testing head used has a electromagnetic ultrasonic transducer (1) having a magnetic field source (2) and a magnetic field sensor (3), an excitation pulse is transmitted using the ultrasonic transducer (1) to the workpiece (11) to generate an ultrasonic wave, and a response signal is measured using the magnetic field sensor (3), testing information, preferably transit time information of the ultrasonic wave and therefrom wall thickness information about the thickness of the workpiece (11) being ascertained on the basis of an ultrasonic echo component of the response signal measured by the magnetic field sensor (3), and further information, wherein wall thickness information and distance information about the distance of the testing head from the workpiece (11), being ascertained on the basis of a magnetic field component of the response signal measured by the magnetic field sensor (3), and wherein the testing head used has an excitation coil (4), using which the excitation pulse is generated, the magnetic field component used to ascertain the further information, in particular the distance information, containing an alternating field component of an alternating field generated by the excitation coil and the alternating field component being analyzed to ascertain the distance information.

* * * * *